United States Patent [19]

Dalgaard

[11] Patent Number: 4,471,296
[45] Date of Patent: Sep. 11, 1984

[54] MEASURING OXYGEN CONCENTRATION

[75] Inventor: Svend B. Dalgaard, Murrysville, Pa.

[73] Assignee: Westinghouse Electric Corp., Pittsburgh, Pa.

[21] Appl. No.: 324,364

[22] Filed: Nov. 24, 1981

[51] Int. Cl.³ .................................. G01N 27/00
[52] U.S. Cl. ............................. 324/71.1; 73/29; 73/61 R
[58] Field of Search .............. 324/56, 65 CR, 71.1; 73/29, 23, 61 R, 61.1 R, 721, 727, DIG. 4

[56] References Cited

U.S. PATENT DOCUMENTS 3,253,219  5/1966  Littler ........................... 324/71.1
4,180,771  12/1979  Guckel ......................... 324/71.1

Primary Examiner—Michael J. Tokar
Assistant Examiner—Kevin D. O'Shea
Attorney, Agent, or Firm—R. D. Fuerle

[57] ABSTRACT

Disclosed is a device and a method for measuring the partial pressure of oxidizing species in a liquid. A metal or incompletely oxidized metal oxide which is susceptible to anodic oxidation and which forms an oxide having a Pilling-Bedworth ratio greater than one is placed in the liquid. The oxide formed on the metal is confined and the pressure of the confined oxide is measured. That pressure is a known function of the concentration of oxidizing species in the liquid. The device is calibrated in liquids of known oxygen content to establish the relationship between oxide content and pressure.

10 Claims, 2 Drawing Figures

MEASURING OXYGEN CONCENTRATION

BACKGROUND OF THE INVENTION

Oxygen dissolved in water, even in extremely low concentrations, can cause severe corrosion problems for various metals. At a level of only one part per billion the corrosion potential of oxygen is significant, and it is sufficient to corrode many metals and alloys in contact with water. For example, oxygen is believed to be responsible, at least in part, for the cracking which occurs in the keyways of steam turbines, the denting of nuclear boiler tubing, and the pitting which can occur in fossil fuel boilers and associated equipment.

Oxygen corrosion can be reduced by metering various oxygen scavengers, such as hydrazine, into the water. However, it is necessary to accurately measure the oxygen content of the water to avoid using too little oxygen scavenger, which may result in corrosion, or too much oxygen scavenger, as some scavengers themselves can break down to form various products which can corrode metal if they are used in excess.

The sensitivity of present meters for measuring oxygen, however, is only about one or two parts per billion of oxygen and at that level they are not very accurate. Thus they cannot be relied upon to indicate whether or not oxygen has been adequately reduced to control the corrosion process. Moreover, present oxygen meters are bulky and cannot be used in small spaces such as the core of a nuclear reactor.

SUMMARY OF THE INVENTION

I have invented a method and apparatus for measuring oxygen which is sensitive and precise to a level at least as low as 0.001 ppb. The oxygen measuring device of this invention is simple, easy to make, reliable, and reusable. It is also small enough so that it can be placed in the core of a nuclear reactor and in other confined spaces to measure the various oxidizing species which are present.

The device of this invention will measure the partial pressure of any oxidizing species although most commonly oxygen is the only oxidizing species that is present, except for the in-core coolant in nuclear reactors.

PRIOR ART

Littler U.S. Pat. No. 3,253,219 discloses a method of determining the corrosion rate by measuring the change in the frequency of a piezoelectric crystal which is positioned next to a corrodable specimen.

DESCRIPTION OF THE PREFERRED EMBODIMENT

Figure 1:
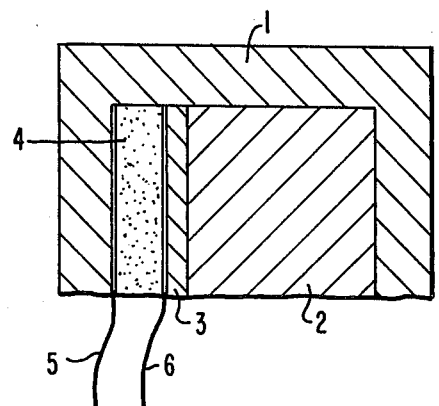
FIG. 1 is a side view of a certain presently preferred embodiment of an oxygen meter probe according to this invention.

In FIG. 1 a clamp 1 of a strong and inert material confines an oxide producing metal 2, the oxide 3 produced when said metal oxidizes, and a pressure measuring device 4. An electrical potential is generated in wires 5 and 6 in proportion to the pressure exerted against pressure measuring device 4.

Figure 2:
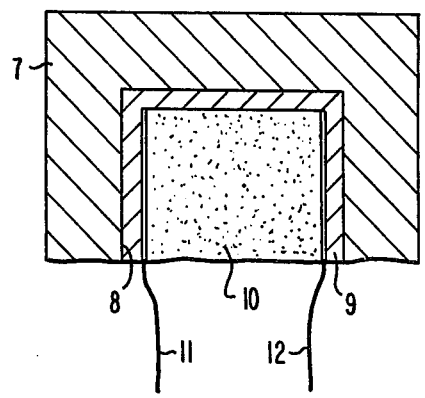
FIG. 2 is a side view of another certain presently preferred embodiment of an oxygen meter probe according to this invention.

In FIG. 2 an oxide producing metal 7 has an opening 8 in which is contained the oxide 9 of the metal and a pressure measuring device 10. Wires 11 and 12 carry the electrical potential generated by pressure measuring device 10.

When the oxygen measuring probe is placed in the liquid the oxygen content of which is to be measured, an electrochemical cell is formed such that the surface of the oxide producing metal becomes anodic. As a result an oxide is formed, the pressure of which on the pressure measuring device is a known function of the oxygen concentration in the liquid. When the device is first placed in the liquid it is necessary to permit a period of time to pass in order for the oxide layer to reach equilibrium with the amount of oxygen in the solution.

The clamp shown in FIG. 1 may be made of any inflexible inert material such as platinum or another noble metal. It can also be entirely eliminated, as shown in FIG. 2, by positioning the oxide and pressure measuring device within an orifice in the oxide forming metal itself.

The oxide forming metal must have a Pilling-Bedworth ratio of greater than 1. The Pilling-Bedworth ratio is the volume of the oxide of the metal divided by the volume of the metal, so that a ratio greater than one means that the oxide takes up more space than does the metal itself and will therefore exert a pressure on the pressure measuring device. If the oxygen measuring device is to be used to measure relatively high levels of oxygen the oxide forming metal should have an oxide of low free energy, such as the oxide of nickel or copper. If the oxygen measuring device is to be used to measure levels of oxygen at lower concentrations the free energy of the oxide should be higher, such as the oxides of iron. The oxide forming metal must be susceptible to anodic oxidation in the liquid. Any metal or incompletely oxidized metal oxide which has a Pilling-Bedworth ratio in excess of 1 and which is susceptible to anodic oxidation could be used in this invention. No particular thickness or area for the oxide forming material is required, however.

The pressure measuring device is preferably a piezoelectric semiconductor but other devices which measure pressure could also be used.

The liquid in which the oxygen measuring device is placed is typically water as that liquid is widely used in industrial processes and presents the greatest corrosion problems. However, the device may also be suitable for use in other liquids.

Before the oxygen measuring device is used to determine the oxygen content of a liquid it must first be calibrated. Calibration is accomplished by measuring the pressures which result when the device is placed in liquids of known oxygen content. There are many ways that liquids of known oxygen content can be prepared. First, if the liquid is water it can be boiled to reduce the oxygen content to zero, and then the water can be doped with nitrogen containing a known amount of oxygen. Another procedure for producing samples of water containing known quantities of oxygen is to add copper or nickel to oxygen containing water. The water is permitted to sit until an equilibrium partial pressure of oxygen is reached. The oxygen content at that equilibrium level is known in the art.

I claim:

1. A device for measuring the partial pressure of oxidizing species in a liquid comprising (1) a substance which is susceptible to anodic oxidation and which forms an oxide having a Pilling-Bedworth ratio greater than 1, selected from the group consisting of metals, incompletely oxidized metal oxides, and mixtures thereof;

(2) means for confining said oxide as it is formed on said substance; and (3) means for measuring the pressure of said confined oxide.

2. A device according to claim 1 wherein said substance is a metal.

3. A device according to claim 2 wherein said metal is selected from the group consisting of iron, alloys of iron, and mixtures thereof.

4. A device according to claim 2 wherein said metal is selected from the group consisting of copper, nickel, alloys thereof, and mixtures thereof.

5. A device according to claim 2 wherein said means for confining said oxide is a space within said metal.

6. A device according to claim 2 wherein said means for confining said oxide is an inert, inflexible clamp which confines said oxide between said metal and said means for measuring the pressure of said confined oxide.

7. A device according to claim 1 wherein said liquid is water.

8. A device according to claim 1 wherein said means for measuring pressure is a semiconductor.

9. A method of measuring the oxygen content of a liquid having unknown oxygen content comprising (1) placing into samples of said liquid having known oxygen contents a device which comprises;
  (a) a substance which is susceptible to anodic oxidation and which forms an oxide having a Pilling-Bedworth ratio greater than 1, selected from the group consisting of metals, incompletely oxidized metal oxides, and mixtures thereof;
  (b) means for confining said oxide as it is formed on said substance; and
  (c) means for measuring the pressure of said confined oxide;

(2) measuring the pressure of said confined oxide at said oxygen contents to obtain a relationship between said pressure and said oxygen content;

(3) placing said device or an identically constructed device in said liquid of unknown oxygen content;

(4) measuring the pressure of said confined oxide in said liquid;

(5) matching said pressure with oxygen content according to said previously determined relationship.

10. A method of measuring the oxygen content of a liquid having unknown oxygen content comprising (1) placing in a liquid a substance which is susceptible to anodic oxidation and which forms an oxide having a Pilling-Bedworth ratio greater than 1, selected from the group consisting of metals, incompletely oxidized metals oxides, and mixtures thereof;

(2) confining said oxide as it is formed on said substance and (3) measuring the pressure of said confined oxide.

* * * * *